United States Patent
Lee et al.

(10) Patent No.: US 9,518,035 B2
(45) Date of Patent: Dec. 13, 2016

(54) METHOD FOR PREPARING GLYCIDOL USING GLYCEROL AND GLYCIDOL OBTAINED THEREBY

(71) Applicant: KOREA INSTITUTE OF SCIENCE AND TECHNOLOGY, Seoul (KR)

(72) Inventors: Hyun Joo Lee, Seoul (KR); Byoung Sung Ahn, Seoul (KR); Sang Deuk Lee, Seoul (KR); Ji Sik Choi, Seoul (KR); Hyejeong Lee, Seoul (KR); Hye Jin Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/015,890

(22) Filed: Feb. 4, 2016

(65) Prior Publication Data

US 2016/0244419 A1    Aug. 25, 2016

(30) Foreign Application Priority Data

Feb. 23, 2015    (KR) .................. 10-2015-0025338

(51) Int. Cl.
*C07D 301/02*    (2006.01)
*C07D 317/20*    (2006.01)

(52) U.S. Cl.
CPC ........... *C07D 301/02* (2013.01); *C07D 317/20* (2013.01)

(58) Field of Classification Search
CPC ........................ C07D 301/02; C07D 317/20
USPC ........................................................ 549/518
See application file for complete search history.

(56) References Cited

U.S. PATENT DOCUMENTS

| | | | |
|---|---|---|---|
| 2,856,413 A | 10/1958 | Malkemus et al. | |
| 5,359,094 A | 10/1994 | Teles et al. | |
| 6,025,504 A | 2/2000 | Claude et al. | |
| 7,888,517 B2 | 2/2011 | Uno et al. | |
| 2009/0318718 A1* | 12/2009 | Uno | C07D 301/02 549/518 |

FOREIGN PATENT DOCUMENTS

| | | |
|---|---|---|
| JP | 2007-039347 A | 2/2007 |
| JP | 2008-285457 A | 11/2008 |
| JP | 2009-067689 A | 4/2009 |
| JP | 2009-137938 A | 6/2009 |
| JP | 5123852 B | 11/2012 |
| KR | 1020120114088 B1 | 10/2012 |

OTHER PUBLICATIONS

Sonnati et al, Glycerol carbonate as a versatile building block for tomorrow; synthesis, reactivity, properties and applications, Green Chem., 2013, 15, p. 283-306.*
Choi et al. Ionic-liquid-catalyzed decarboxylation of glycerol carbonate to glycido, Journal of Catalysis, Nov. 17, 2012, pp. 248-255, 297(2013), Elsevier.
Sandhya et al. Comparative Efficacy of Polyamine-Based Scavenger Rains, International Journal of Organic Chemistry, Feb. 2, 2012, pp. 71-74, vol. 2, Scientific Research.

* cited by examiner

*Primary Examiner* — T. Victor Oh
(74) *Attorney, Agent, or Firm* — Goldilocks Zone IP Law

(57) ABSTRACT

A method for preparing glycidol using glycerol includes mixing glycerol with urea in the presence of at least one zinc-based catalyst selected from the group consisting of $Zn(NO_3)_2$, $ZnCl_2$, $ZnO$ and $Zn(OAc)_2$ under a pressure of 0.5-10 kPa at a temperature of 100-170° C. to obtain glycerol carbonate; filtering the glycerol carbonate mixed with the zinc-based catalyst through an adsorbent including a polymer resin coordinated with amine groups to separate the zinc-based catalyst and glycerol carbonate from each other; and carrying out reaction of the glycerol carbonate separated from the zinc-based catalyst in the presence of an anion alkali metal salt catalyst that is Na, K, Rb, Cs or a mixture thereof containing at least one anion selected from the group consisting of $Cl^-$, $Br^-$, $I^-$, $NO_3^-$, $NO_2^-$ and acetate under a pressure of 0.13-6.67 kPa at a temperature of 140-250° C. to obtain glycidol.

10 Claims, No Drawings

METHOD FOR PREPARING GLYCIDOL USING GLYCEROL AND GLYCIDOL OBTAINED THEREBY

CROSS-REFERENCE TO RELATED APPLICATIONS

This application claims priority under 35 U.S.C. §119 to Korean Patent Application No. 10-2015-0025338 filed on Feb. 23, 2015 in the Korean Intellectual Property Office, the disclosure of which is incorporated herein by reference in its entirety.

TECHNICAL FIELD

The following disclosure relates to a method for preparing glycidol from glycerol with high yield and selectivity through a simple reaction process, and glycidol obtained thereby.

BACKGROUND

Glycidol is an important raw material raw for polyglycerin, glycerol ester, dihydroxy propylamine, UV curing agent for perfumery and cosmetics, a detergent, drugs, a coating and semiconductors. Glycidol has been synthesized industrially by a method including oxidizing allyl alcohol by using hydrogen peroxide in the presence of a catalyst and a method including treating chloropropanediol with a base. However, although the above methods provide high production yield, these process suffer from the drawbacks such as 1) multistep synthesis which decreases the synthetic efficiency as well as increases the production cost and 2) produce large amount of waste water and salt.

Another method for preparing glycidol includes carrying out thermal decomposition of glycerol carbonate obtained from glycerol, as shown in following reaction.

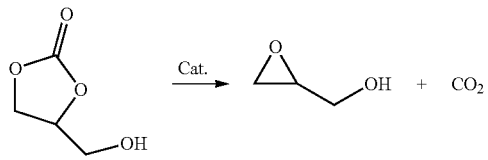

Thermal decomposition of glycerol carbonate is catalyzed by a metal salt catalyst and produce glycidol and carbon dioxide.

Glycerol is a renewable and cheap raw material, which is coproduced from bio-diesel production from vegetable oil or animal fat. These days, the increasing demand for biodiesel resulted in the byproduct glycerol available in large quantities at low price. Accordingly, synthesis of Glycidol from the glycerol carbonate which can be made from glycerol is worthy to be developed in the aspect of cost-efficiency and eco-friendly characteristics.

Meanwhile, as a method for preparing glycerol carbonate that is an intermediate from glycerol, there has been known a method using $CO_2$, dimethyl carbonate, urea, or the like. In the case of a method that uses urea, it has high cost-efficiency and provides glycerol carbonate with relatively high yield. Japanese Laid-open Patent No. 2008-285457 discloses a method for preparing glycerol carbonate by using anhydride, such as $MnSO_4$. Japanese Laid-open Patent No. 2007-039347 discloses a method for preparing glycerol carbonate by using $MgSO_4$ as catalyst. In addition, U.S. Pat. No. 6,025,504 discloses use of a sulfide of Mn, Mg, Fe, Ni or Cd as catalyst, and Korean Patent Publication No. 1307559 discloses a method for preparing glycerol carbonate by reacting glycerol with urea in the presence of a Zn catalyst coordinated with halide-based and nitrate-based ligands. The above-mentioned documents disclose methods for preparing glycerol carbonate based on urea. However, there is no description about a method for preparing glycidol starting from the produced glycerol carbonate.

Meanwhile, Japanese Laid-open Patent Nos. 2009-137938 and 2009-067689 disclose a method that includes preparing glycerol carbonate by using a Lewis acid catalyst, such as $ZnSO_4$. Then, the product was distilled using thin film distillation unit at 150-180° C. under 0.06-0.7 kPa for the removal of zinc catalyst, a Lewis acid, which functions as catalyst during the the decarboxylation of glycerol carbonate for the synthesis of glycidol. Actually, many documents report that a catalyst having a Lewis base type anion is used as catalyst for decarboxylation of glycerol carbonate.

U.S. Pat. No. 2,856,413 discloses a method that uses a phosphate or carbonate base compound. U.S. Pat. Nos. 5,359,094 and 7,888,517 disclose a method that uses a sulfate, halide or acetate compound. In addition, use of ionic liquid-based nitrate is disclosed in *Journal of Catalysis* 297, (2013), 248-225. The above-mentioned anionic or Lewis base-type catalysts lose their anionic characteristics through acid-base reaction when a Lewis acid is present in the reaction mixture, resulting in loss of catalytic activity.

Therefore, in the reaction of preparing glycidol from glycerol by way of glycerol carbonate, it is important to remove the catalyst used for the preceding reaction or to purify glycerol carbonate through distillation or the like.

A typical method for removing a catalyst for use in preparing glycerol carbonate includes the above-mentioned thin layer distillation method. Although the thin layer distillation method is useful for overcoming the high boiling point of glycerol carbonate and thermal unstability thereof, it requires a high distillation temperature and a high vacuum degree, leading to high energy consumption and increased cost of equipment in a process for preparing glycidol.

As a result, there has been a need for a method for preparing glycidol from glycerol by a simple process, while reducing energy consumption and cost of equipment.

SUMMARY

An embodiment of the present disclosure is directed to providing a method for preparing glycidol with high yield and selectivity through a simple reaction process from glycerol, the method including removing a catalyst present in a solution after preparing glycerol carbonate by using a polymer resin having a tertiary amine group.

Another embodiment of the present disclosure is directed to providing glycidol obtained by the above-mentioned method.

In one aspect, there is provided a method for preparing glycidol, including the steps of: (A) mixing glycerol with urea in the presence of at least one zinc-based catalyst selected from the group consisting of $Zn(NO_3)_2$, $ZnCl_2$, ZnO and $Zn(OAc)_2$ under a pressure of 0.5-10 kPa at a temperature of 100-170° C. to obtain glycerol carbonate; (B) filtering the glycerol carbonate mixed with the zinc-based catalyst through an adsorbent including a polymer resin coordinated with amine groups to separate the zinc-based catalyst and glycerol carbonate from each other; and (C) carrying out reaction of the glycerol carbonate separated from the zinc-based catalyst in the presence of an anion alkali metal salt catalyst that is Na, K, Rb, Cs or a mixture thereof containing at least one anion selected from the group consisting of $Cl^-$, $Br^-$, $I^-$, $NO_3^-$, $NO_2^-$ and acetate under a pressure of 0.13-6.67 kPa at a temperature of 140-200° C. to obtain glycidol.

According to an embodiment, the amine group in step (B) may be selected from the group consisting of ethylenediamine, diethylenetriamine and triethylenetetramine, and the polymer resin may be Merrifield resin or Wang resin.

According to another embodiment, urea may be mixed with glycerol at a ratio of 1-5 moles per mole of glycerol, in step (A).

According to still another embodiment, the zinc-based catalyst may be mixed in an amount of 0.1-5 mole % based on glycerol, in step (A).

According to still another embodiment, the adsorbent may be a polymer resin containing amine groups, in step (B).

According to still another embodiment, the anion alkali metal salt catalyst may be used in an amount of 0.1-5 mole % based on glycerol carbonate, in step (C).

According to yet another embodiment, step (C) may be carried out in a continuous reaction mode in which glycidol is recovered continuously under reduced pressure.

In another aspect, there is provided glycidol obtained by the method disclosed herein.

The method for preparing glycidol disclosed herein uses a zinc-based catalyst when preparing glycerol carbonate from glycerol, while using an anion alkali metal salt catalyst when preparing glycidol from the glycerol carbonate, and thus provides glycidol with high yield and selectivity.

In addition, the method for preparing glycidol disclosed herein uses an adsorbent instead of a thin layer distillation method requiring a thin layer distillation device according to the related art. Then, the glycerol carbonate filtered through the adsorbent is allowed to react with an anion alkali metal salt catalyst to obtain glycidol. As a result, it is possible to obtain glycidol from glycerol through a simple process, and thus to reduce the cost and time required for the overall process significantly.

DETAILED DESCRIPTION OF EMBODIMENTS

The present disclosure relates to a method for preparing glycidol from glycerol with high yield and selectivity through a simple reaction process and glycidol obtained thereby.

Particularly, the present disclosure relates to a method for preparing high added-value glycidol from glycerol generated during the production of bio-diesel as byproduct by an effective linkage of the two steps of forming glycerol carbonate from glycerol and forming glycidol from glycerol carbonate.

Hereinafter, the present disclosure will be explained in more detail.

The method for preparing glycidol disclosed herein includes reacting glycerol with urea in the presence of a catalyst to obtain glycerol carbonate, which, in turn, is subjected to decarboxylation to obtain glycidol, as depicted in the following Reaction Scheme 1:

[Reaction Scheme 1]

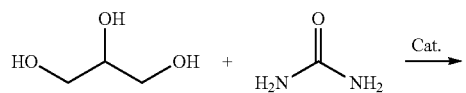

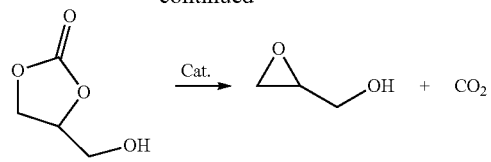

-continued

Particularly, the method for preparing glycidol disclosed herein includes the steps of: (A) mixing glycerol with urea in the presence of a zinc-based catalyst to obtain glycerol carbonate; (B) passing the glycerol carbonate mixed with the zinc-based catalyst through an adsorbent to separate the zinc-based catalyst and glycerol carbonate from each other; and (C) carrying out decarboxylation of the glycerol carbonate separated from the zinc-based catalyst in the presence of an anion alkali metal salt catalyst that is Na, K, Rb, Cs or a mixture thereof containing at least one anion selected from the group consisting of $Cl^-$, $Br^-$, $I^-$, $NO_3^-$, $NO_2^-$ and acetate to obtain glycidol.

First, in step (A), glycerol is mixed with urea in the presence of a zinc-based catalyst to obtain glycerol carbonate.

There is no particular limitation in the zinc-based catalyst, as long as it does not adversely affect the catalyst added in the subsequent step (C). Particularly, the zinc-based catalyst may be at least one selected from the group consisting of $Zn(NO_3)_2$, $ZnCl_2$, $ZnO$ and $Zn(OAc)_2$.

Urea is mixed with glycerol at a ratio of 1-5 moles, particularly 1-2 moles of urea per mole of glycerol. When the amount of urea is less than the lower limit based on glycerol, it is not possible to produce glycerol carbonate. When the amount of urea is larger than the upper limit, a large amount of byproduct is produced, resulting in a decrease in yield.

In addition, the zinc-based catalyst is used in an amount of 0.1-5 mole %, particularly 1-3 mole %, based on glycerol. When the amount of zinc-based catalyst is less than the lower limit, reaction time is increased, resulting in production of byproduct. When the amount of zinc-based catalyst is larger than the upper limit, there is no further improvement in reaction time, reaction rate and yield.

Glycerol is allowed to react with urea in the presence of the zinc-based catalyst under a pressure of 0.5-10 kPa, particularly 2-4 kPa; at a temperature of 100-170° C., particularly 140-160° C.; for a reaction time of 30 minutes to 5 hours, particularly 1-3 hours to produce glycerol carbonate.

When the pressure is beyond the above-defined range, it is not possible to carry out reaction.

In addition, when the temperature is less than the lower limit, glycerol carbonate may be produced with low yield. When the temperature is higher than the upper limit, production of byproduct may be increased.

Further, when the reaction time is shorter than the lower limit, glycerol carbonate may be produced with low yield. When the reaction time is longer than the upper limit, there is no further improvement in yield.

Next, in step (B), glycerol carbonate mixed with the zinc-based catalyst is filtered through an adsorbent to separate the zinc-based catalyst and glycerol carbonate from each other.

As adsorbent, a polymer resin including (coordinated with) amine groups may be used. There is no particular limitation in the polymer resin, as long as it has at least two amine groups in its molecule and one of the terminal amines has at least one hydrogen atom. Particular examples of the amine include ethylenediamine, diethylenetriamine or triethylenetetramine. In addition, particular examples of the polymer resin include Merrifield resin or Wang resin. Herein, amine groups are present on the polymer resin surface at a concentration of 1.5-4 mmol/g.

For example, the polymer resin as adsorbent may be prepared by combining Merrifield resin with an amine compound, as depicted in the following Reaction Scheme 2:

[Reaction Scheme 2]

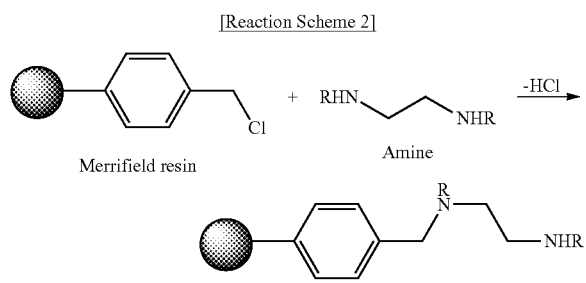

When using a general adsorbent other than the above-mentioned adsorbent, such as active carbon, alumina, silica or molecular sieve, the affinity between glycerol carbonate and a metal catalyst is larger than the affinity between the adsorbent and a metal catalyst, and thus the adsorption quality to the metal catalyst is not high.

According to the related art, glycerol carbonate is purified through thin layer distillation requiring a special distillation device. However, according to the present disclosure, substantially pure glycerol carbonate is separated simply by using the adsorbent. Thus, in the subsequent step, it is possible to produce glycidol with higher yield and selectivity as compared to the conventional methods and to reduce cost and time.

When the adsorbent is not used and thus glycerol carbonate still containing the zinc-based catalyst is subjected to decarboxylation in the presence of an anion alkali metal salt catalyst, the catalytic activity of alkali metal salt is degraded and the reaction cannot proceed, resulting in a failure in continuous recovery of glycidol and degradation of cost-efficiency.

Then, in step (C), glycerol carbonate separated from the zinc-based catalyst is subjected to decarboxylation in the presence of an anion alkali metal salt catalyst to obtain glycidol.

Particularly, Na, K, Rb, Cs or a mixture thereof containing at least one anion selected from the group consisting of Cl$^-$, Br$^-$, I$^-$, NO$_3^-$, NO$_2^-$ and acetate is used as anion alkali metal salt catalyst in order to obtain high yield and selectivity.

Even though the adsorbent is used in step (B), glycerol carbonate used as a starting material for step (C) still contains a trace amount of zinc-based catalyst. When preparing glycidol in the presence of the zinc-based catalyst, use of a catalyst other than the anion alkali metal salt catalyst leads to a failure in production of glycidol or degradation of yield and selectivity. In addition, use of an ionic material containing such anion alone leads to generation of a large amount of byproduct.

The anion alkali metal salt catalyst is used in an amount of 0.1-5 mole %, particularly 0.5-3 mole %, based on glycerol carbonate. When the amount of anion alkali metal salt catalyst is less than the lower limit, reaction conversion may be degraded. When the amount of anion alkali metal salt catalyst is larger than the upper limit, there is no further improvement in reaction yield and rate.

In addition, glycerol carbonate is subjected to decarboxylation under a pressure of 0.13-6.67 kPa, particularly 2-4 kPa; at a temperature of 140-250° C., particularly 160-220° C., to obtain glycidol.

When the pressure is less than the lower limit, the selectivity to glycidol is degraded and continuous reaction may not be carried out. When the pressure is higher than the upper limit, the reaction rate may be decreased.

In addition, when the temperature is less than the lower limit, yield of glycidol may be decreased. When the temperature is higher than the upper limit, selectivity to glycidol may be degraded.

Particularly, step (C) produces glycidol through decarboxylation as well as leads to concentration of the catalyst in the reactor as the reaction proceeds, thereby increasing the possibility of side reaction. Therefore, in order to inhibit such side reaction effectively, it is preferred to carry out decarboxylation in a continuous reaction mode in which glycidol is recovered continuously.

The examples and experiments will now be described. The following examples and experiments are for illustrative purposes only and not intended to limit the scope of this disclosure. It will be apparent to those skilled in the art that various changes and modifications may be made without departing from the spirit and scope of the disclosure as defined in the following claims

PREPARATION EXAMPLE 1

Preparation of Adsorbent

Merrifield resin (Cl content: 2 mmol/g) is mixed with ethylenediamine at a molar ratio of 1:1 in the presence of acetonitrile as solvent, followed by boiling for 3 hours. After the reaction, the reaction mixture is washed with aqueous NaOH solution (3 wt %) and methanol and vacuum dried to obtain an adsorbent. The resultant resin is analyzed for its amine content and the amine content is shown to be 5.3% (1.9 mmol diamine/g resin).

PREPARATION EXAMPLE 2

Preparation of Adsorbent

An adsorbent is obtained in the same manner as Preparation Example 1, except that diethylenetriamine is used instead of ethylenediamine.

EXAMPLE 1

Preparation of Glycidol

First, 23 g (0.25 moles) of glycerol, 15 g (0.25 moles) of urea, 1.50 g (2 mole % based on glycerol) of Zn(NO$_3$)$_2$.6H$_2$O are introduced to a flask and agitated at 150° C. under 2.67 kPa for 2 hours to obtain a solution of glycerol carbonate, which, in turn, is passed through the adsorbent obtained according to Preparation Example 1. To the solution of glycerol carbonate from which the Zn(NO$_3$)$_2$ catalyst is removed, NaNO$_3$ catalyst is added in an amount of 1 mole % based on glycerol carbonate and reaction is carried out at 175° C. under 2.67 kPa. Then, the produced glycidol is recovered continuously.

EXAMPLE 2

Preparation of Glycidol

Glycidol is obtained in the same manner as Example 1, except that the adsorbent obtained according to Preparation Example 2 is used.

COMPARATIVE EXAMPLE 1

Preparation of Glycidol Using No Adsorbent

Glycidol is obtained in the same manner as Example 1, except that any adsorbent is not used but glycerol carbonate containing the $Zn(NO_3)_2$ catalyst is used for the subsequent reaction.

COMPARATIVE EXAMPLE 2

Preparation of Glycidol Using No Adsorbent and Using Excessive $NaNO_3$ Catalyst Glycidol is obtained in the same manner as Example 1, except that any adsorbent is not used but $NaNO_3$ as catalyst is used in an amount of 10 mole % based on glycerol carbonate.

COMPARATIVE EXAMPLE 3

Preparation of Glycidol Using Alumina as Adsorbent

Glycidol is obtained in the same manner as Example 1, except that alumina is used as adsorbent.

COMPARATIVE EXAMPLE 4

Preparation of Glycidol Using Zeolite as Adsorbent

Glycidol is obtained in the same manner as Example 1, except that zeolite is used as adsorbent.

TEST EXAMPLE 1

Determination of Yield and Selectivity

The yield and selectivity of glycidol obtained from each of the above Examples and Comparative Examples are calculated according to the following Mathematical Formula 1 and Mathematical Formula 2.

Yield (%)=amount of glycidol product/amount of glycerol before reaction×100 [Mathematical Formula 1]

Selectivity (%)=amount of glycidol product/amount of glycerol converted after reaction×100 [Mathematical Formula 2]

TABLE 1

|  | Ex. 1 | Ex. 2 | Comp. Ex. 1 | Comp. Ex. 2 | Comp. Ex. 3 | Comp. Ex. 4 |
|---|---|---|---|---|---|---|
| Yield (%) | 64.8 | 63.7 | 11.5 | 44.2 | 20.5 | 21.7 |
| Selectivity (%) | 86.3 | 69.9 | 11.8 | 56.1 | 21.6 | 22.7 |

As shown in Table 1, Examples 1 and 2 according to the present disclosure provide higher yield and selectivity of glycidol as compared to the methods according to Comparative Examples 1-4. Particularly, when using a polymer resin coordinated with amine groups as adsorbent, the yield and selectivity are higher as compared to the method using no adsorbent or using the other types of adsorbents.

What is claimed is:

1. A method for preparing glycidol, comprising the steps of:
   (A) mixing glycerol with urea in the presence of a zinc-based catalyst to obtain glycerol carbonate;
   (B) filtering the glycerol carbonate mixed with the zinc-based catalyst through an adsorbent including a polymer resin coordinated with amine groups to separate the zinc-based catalyst and glycerol carbonate from each other; and
   (C) carrying out reaction of the glycerol carbonate separated from the zinc-based catalyst in the presence of an anion alkali metal salt catalyst to obtain glycidol.

2. The method for preparing glycidol according to claim 1, wherein the amine group in step (B) is selected from the group consisting of ethylenediamine, diethylenetriamine and triethylenetetramine.

3. The method for preparing glycidol according to claim 1, wherein the polymer resin in step (B) is Merrifield resin or Wang resin.

4. The method for preparing glycidol according to claim 1, wherein the adsorbent in step (B) comprises amine groups present in the polymer resin at a concentration of 1.5-4 mmol/g.

5. The method for preparing glycidol according to claim 1, wherein the zinc-based catalyst in step (A) is at least one selected from the group consisting of $Zn(NO_3)_2$, $ZnCl_2$, ZnO and $Zn(OAc)_2$.

6. The method for preparing glycidol according to claim 1, wherein urea is mixed with glycerol at a ratio of 1-5 moles per mole of glycerol, in step (A).

7. The method for preparing glycidol according to claim 1, wherein the zinc-based catalyst is mixed in an amount of 0.1-5 mole % based on glycerol, in step (A).

8. The method for preparing glycidol according to claim 1, wherein the anion alkali metal salt catalyst in step (C) is Na, K, Rb, Cs or a mixture thereof containing at least one anion selected from the group consisting of $Cl^-$, $Br^-$, $I^-$, $NO_3^-$, $NO_2^-$ and acetate.

9. The method for preparing glycidol according to claim 1, wherein the anion alkali metal salt catalyst is used in an amount of 0.1-5 mole % based on glycerol carbonate, in step (C).

10. The method for preparing glycidol according to claim 1, wherein step (C) is carried out in a continuous reaction mode in which glycidol is recovered continuously under reduced pressure.

* * * * *